United States Patent
Kunkel et al.

(10) Patent No.: US 6,206,855 B1
(45) Date of Patent: Mar. 27, 2001

(54) HAND AND FINGER GUARD SHIELD FOR MEDICAL USE

(76) Inventors: Melissa A. Kunkel; Gary T. Kunkel, both of 28944 Sam Pl., Canyon Country, CA (US) 91351

( * ) Notice: Subject to any disclaimer, the term of this patent is extended or adjusted under 35 U.S.C. 154(b) by 0 days.

(21) Appl. No.: 09/412,526

(22) Filed: Oct. 5, 1999

Related U.S. Application Data

(60) Provisional application No. 60/103,367, filed on Oct. 7, 1998.

(51) Int. Cl.$^7$ .............................. A61M 5/32; B65D 83/10
(52) U.S. Cl. ........................... 604/192; 206/365; 604/263
(58) Field of Search .................................... 604/192, 263, 604/110; 206/365, 366

(56) References Cited

U.S. PATENT DOCUMENTS

| | | | |
|---|---|---|---|
| 4,610,667 | * | 9/1986 | Pedicano et al. ............... 604/192 |
| 4,623,336 | * | 11/1986 | Pedicano et al. ............... 604/192 |
| 4,747,835 | * | 5/1988 | Sandhaus ........................ 604/192 |
| 4,781,697 | * | 11/1988 | Slaughter ....................... 604/192 |
| 4,900,309 | * | 2/1990 | Netherton et al. ............. 604/192 |
| 4,986,817 | * | 1/1991 | Code ............................... 604/192 |
| 5,000,742 | * | 3/1991 | Morrison ........................ 604/192 |
| 5,067,944 | * | 11/1991 | Nichols .......................... 604/192 |
| 6,059,758 | * | 5/2000 | Padilla et al. .................. 604/263 |

\* cited by examiner

*Primary Examiner*—Bryon P. Gehman
(74) *Attorney, Agent, or Firm*—Roger A. Marrs

(57) ABSTRACT

A shield taking the form of a funnel-like member having a circular peripheral edge defining an enlarged entrance leading into the interior of the funnel to terminate in an elongated attachment portion at its opposite end. The circular edge defining the entrance into the funnel includes a linear edge for prevention of rolling on a flat surface. The attachment portion includes an inner tapered passageway intended to slidably receive and retain a sleeve protector or cover used to enclose a needle to a syringe or hypodermic device. The syringe body holding the needle is intended to reside within the major interior length of the funnel-like member while the needle resides in the protector or cover so that the entire assembled unit can be discarded.

1 Claim, 1 Drawing Sheet

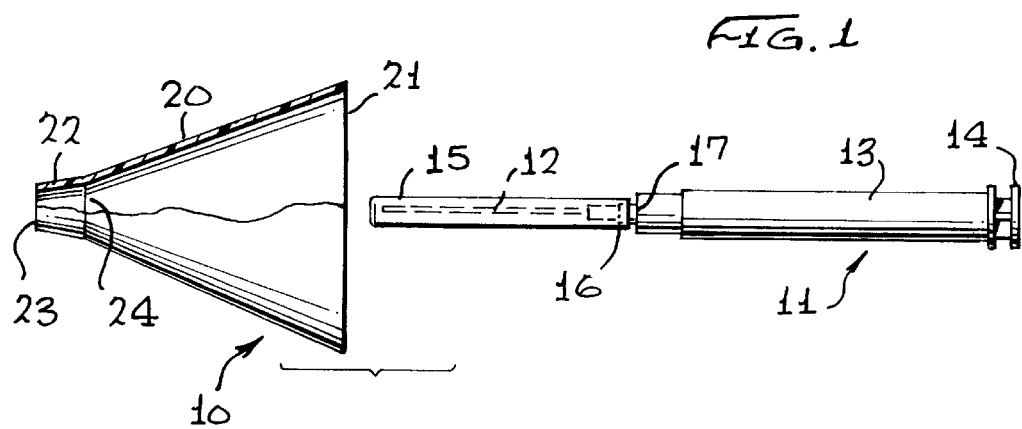
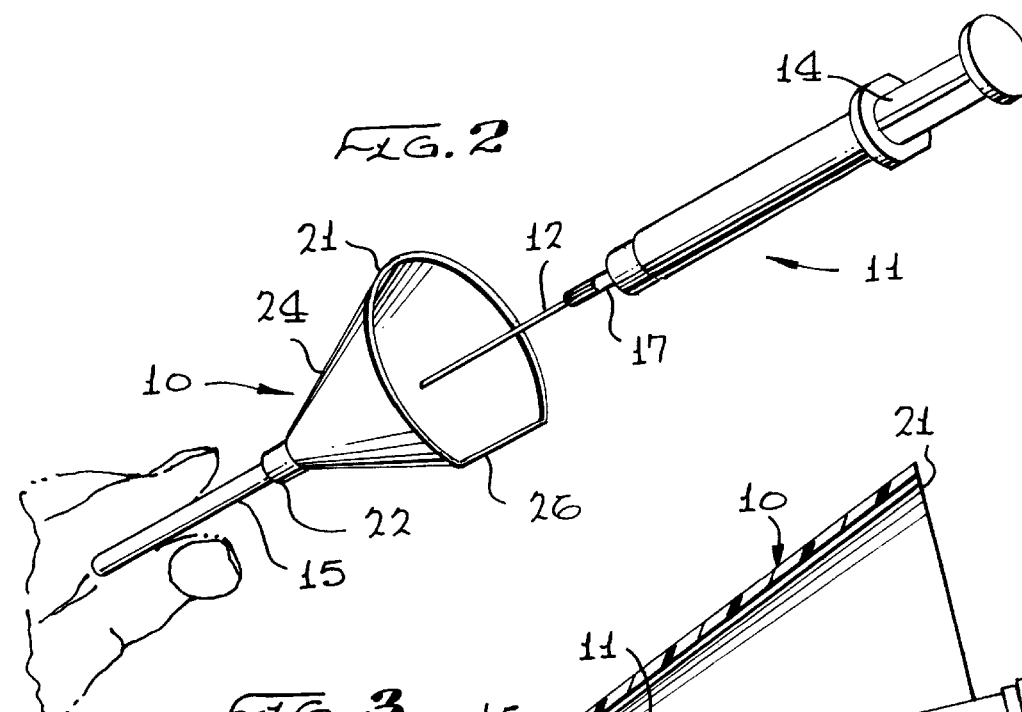

HAND AND FINGER GUARD SHIELD FOR MEDICAL USE

This application claims the benefit of U.S. Provisional Application Ser. No. 60/103,367, filed Oct. 7, 1998.

BACKGROUND OF THE INVENTION

1. Field of the Invention

The present invention relates to the field of syringe and needle disposal devices, and more particularly to a novel finger and hand shield or protector which is insertably mounted over a conventional needle protector while the needle is mounted on a syringe preparatory for disposal of the syringe, needle, needle protector and shield as a unitary construction.

2. Brief Description of the Prior Art

In the medical field, it has been the conventional practice for physicians and medical personnel to dispose of syringes having contaminated needles by tossing the syringe and needle into a bin, box or other container for ultimate disposal. However, once the conventional sleeve protector or sheath has been removed from the needle, the handling of the syringe with an exposed needle is hazardous to medical personnel and a current need has existed to provide a device for reducing the hazard involved in the disposal of conventional syringes and hypodermic needles used throughout the medical world. After the syringe has been used, it is the customary practice to replace the sleeve protector over the used needle and then the entire unit is disposed of by tossing into a suitable container or bag. However, problems and difficulties have been encountered when aligning with and inserting the needle into the sleeve protector which stem largely from the fact that the protector is having a narrow or reduced diameter bore of cylindrical construction. It is easy for the needle to be misaligned with the bore or receptacle within the protector so that the needle progresses externally of the protector to strike or stab the fingers of the medical personnel holding the sleeve protector.

Attempts have been made to use a funnel-like member for directing the forward movement of the needle directly into a protected sheath during a sheathing procedure. Such a device is disclosed in U.S. Pat. No. 4,485,918. However, the device requires an elongated tube integrally formed with and downward depending from the funnel-like member which serves as a holder for the needle protective sheath. The tube is closed at one end so that the sheath is contained in the tube. Thus, the device is expensive to manufacture and requires unnecessary components which necessitates critical dimensioning and precision construction.

Therefore, a long-standing need has existed to provide a means for protecting the hand and fingers of medical personnel as they grasp the sleeve protector or sheath when another person or the opposite hand of the user is attempting to align the needle with the receptacle bore in the protector. Also, a need has existed to provide a means whereby a shield or cup-like member will remain at rest on a flat surface so that it will not roll or fall from a table or other working surface.

SUMMARY OF THE INVENTION

Accordingly, the above problems and difficulties are avoided by the present invention which provides a novel shield taking the form of a funnel-like member of frustro-conical configuration having a peripheral edge defining an enlarged entrance into the interior of the funnel-like member so as to terminate in an attachment portion at its opposite end. The circular edge defining the entrance into the funnel-like member includes a linear edge for prevention of rolling on a flat surface. The attachment portion includes an open-ended inner tapered passageway intended to slidably receive a sleeve protector, cover or sheath in an interference type fit. The sleeve, cover or sheath is used to enclose a syringe or hypodermic needle. The syringe handpiece or body is intended to reside within the major interior length of the funnel-like member and the needle resides in the sleeve, cover or sheath so that the entire assembled unit can be conveniently and safely discarded.

A feature of the present invention resides in providing a funnel-like member having a wide opening or mouth through which the needle can be passed or inserted so as to reach the mouth of the passageway in a sleeve protector intended to encase or enclose the needle.

Another object of the present invention is to provide a novel funnel-like member that may readily accept insertion of different size sleeve protectors for hypodermic or syringe type needles and which includes a wide mouth through which the needle may be inserted preparatory for alignment with and insertion into the sleeve protector.

Another object of the present invention is to provide a novel shield or protector for a hypodermic needle which includes a disposable funnel-like member having a flat edge to prevent rolling on a flat surface and which further includes a terminating tapered aperture for insertably receiving and retaining a sleeve protector.

A further object resides in providing a needle disposal device of frustro-conical configuration having a wide mouth entrance for receiving insertion of the needle and a narrow-tapered, open-ended passage for securing a needle holder in position for alignment with the needle and for insertably receiving the aligned needle.

A further object resides in providing a three component disposable unit comprising a funnel-like member surrounding a syringe body having a needle disposed in a protective sleeve whereby the entire unit may be safely transported for hygienic disposal.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is an exploded side-elevational view, partly in section, showing the novel shield or funnel-like protective member incorporating the present invention;

FIG. 2 is a perspective view of the present invention illustrating the protector for fingers and hand being held by the user preparatory for receiving the insertion of a needle syringe or hypodermic needle; and FIG. 3 is a side-elevational view, partly in section, illustrating the combined syringe or hypodermic needle having the needle enclosed in a sleeve protector and further incorporating the funnel-like member so as to provide an assembly suitable for disposal as a unit.

DESCRIPTION OF THE PREFERRED EMBODIMENT

Referring to FIG. 1, the novel hand and finger shield of the present invention is illustrated in the general direction of arrow 10 which is employed in combination with a hypodermic needle or syringe 11. A needle 12 outwardly projects from a cylindrical syringe housing or body 13 which encases a plunger 14 that, when pressed into the housing, causes a medical fluid, product, solution or the like through the needle 12 into the body of a person. However, when the syringe 11 is being prepared for use or is being transferred from one place to another, the needle 12 is covered by an elongated sleeve protector or sheath 15 which includes an elongated recess having an open end into which the needle 12 is inserted. The open end of the sleeve protector 15 is narrowed at numeral 16 so that an interference fit is produced with the end of the housing 13. Such an end is indicated by numeral 17. When the sleeve protector 15 is carried on the syringe, medical personnel handling the syringe are protected against inadvertent stabbing or contact with the needle 12. However, once the needle has been used after the removal of the sleeve protector 15, the needle is contaminated and disposal is required.

Conventionally, disposal is achieved by replacing the sleeve protector 15 over the needle 12 into the interference fit with element or end 17. Once the protector 15 has been installed, the entire syringe, including the needle and protector, may be tossed into a proper disposal receptacle. The problem, however, still exists that in order to place the protector 12 over the needle, great care and aim must be taken so that the end of the needle enters the receptacle through the opening in the protector 15. Therein lies the problem in that the hand or fingers of a person may be stabbed or make contact with a dirty and unclean needle.

In order to avoid such an event, the present invention includes the shield 10 which is frustro-conical or funnel-like in shape, having a tapered wall 20 terminating at one end in an enlarged entrance or opening defined by an edge 21 wherein the wall 20 decreases in diameter to terminate in a fitting 22 which is also of a tapered configuration terminating in a greatly reduced opening defined by edge 23. The tapered fitting 22 joins with the major length of the shield defined by wall 20 at a juncture, indicated by numeral 24. Both the tapered fitting and the tapered shield are hollow and the entire shield represents an open-ended passageway into which the covered needle 12, including the protector 15, can be held after insertion of the needle into the protector. Once the sleeve protector 15 has entered the major opening defined by edge 21, and has been seated in the fitting 22, the syringe with exposed needle 12 is then introduced to the sleeve protector via the shield 10. Since the fitting 22 is tapered, the sleeve protector will engage in an interference fit by its collar 19 so that it will be retained thereon.

Referring now in detail to FIG. 2, it can be seen that the syringe 11 is in an aiming position preparatory for insertion into the shield protector 10 which is pre-assembled with the sleeve protector 15. As the needle 12 enters the interior of the shield, the user's fingers and hand are protected since any misalignment of the end of the needle with the opening in the sleeve protector would cause the needle to engage with the inside surface of wall 24 of the funnel-like member. The user's fingers can grasp the external surface of the sleeve protector 15 as illustrated while it is attached to the fitting portion 22 through the funnel-like shield member 10.

Referring now in detail to FIG. 3, it can be seen that a three component assembly has been produced wherein the assembly comprises the syringe 11, the sleeve protector 15 and the shield 10. The shield is frictionally attached to the end of sleeve protector 15 by an interference fit between the collar 19 at the entrance 16 to the recess in the sleeve protector and the wall 22. The recess is broadly indicated by numeral 25 occupied by the element 17 of the syringe.

In FIGS. 2 and 3, it can be seen that the invention further includes a flat or straight-edge 26 joined with the circular edge 21 of the funnel-like shield member. The purpose of the flat edge 26 is to prevent rolling of the assembly or the funnel-like member when either is placed on a flat surface, such as a table top 27 in FIG. 3.

In view of the foregoing, it can be seen that the shield or finger and hand protector of the present invention provides a simple and economical device and system for protecting the hand and fingers of medical personnel when the needle 12 is to be inserted into the recess or receptacle of the sleeve protector 15. The funnel-like shield member 10 is place on the end of the sleeve 15 and the tip of the needle 12 is inserted through the wide mouth of the funnel-like shield defined by edge 21, and progresses through its interior until the tip enters the recess of the sleeve protector 15. Once assembled, the entire unit can be disposed of in preferred ways.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A guard shield for finger and hand protection of medical personnel comprising:

a funnel member of conical configuration having a wide entrance defined by a semi-circular edge having opposing corners of said semi-circular edge joined by a continuous and uninterrupted linear edge;

said funnel member having an opening of reduced diameter as compared with said wide entrance and with said opening of reduced diameter constituting an apex of said funnel member;

said funnel member having a conical wall with an interior surface defining an open-ended passageway between said wide entrance and said opening of reduced diameter at said apex;

a syringe protector sleeve insertably disposed in and retained in said opening of reduced diameter in an interference fit with a major portion of said syringe protector sleeve exposed beyond said apex;

a needle syringe having an elongated needle disposed in said syringe protector sleeve;

said funnel member further comprising a conical tapered fitting as part of said conical wall adjacent said apex and cantilevered outwardly from said apex;

said conical tapered fitting defining a tapered portion of said passageway insertably receiving and releasably holding said syringe protector sleeve in said interference fit;

said syringe protector sleeve having a collar carried at a selected end thereof and bearing against said tapered portion of said passageway;

said conical tapered fitting retaining said syringe protector sleeve whereby said syringe, said funnel member and said syringe protector sleeve provide a unitary assembly for disposal purposes.

* * * * *